United States Patent [19]

Daughton et al.

[11] Patent Number: 4,506,987
[45] Date of Patent: Mar. 26, 1985

[54] HIGH PRESSURE LIQUID CHROMATOGRAPHIC GRADIENT MIXER

[75] Inventors: Christian G. Daughton, San Pablo; Richard H. Sakaji, El Cerrito, both of Calif.

[73] Assignee: The United States of America as represented by the United States Department of Energy, Washington, D.C.

[21] Appl. No.: 415,946

[22] Filed: Sep. 8, 1982

[51] Int. Cl.³ .......................... B01F 5/04; B01F 13/10; B01F 15/02
[52] U.S. Cl. .................................... 366/160; 366/177; 366/339; 366/341
[58] Field of Search ............... 366/160, 173, 339, 341, 366/177, 150, 176, 338, 134; 137/896, 897, 898; 138/42; 48/189.4, 189.6; 239/487

[56] References Cited

U.S. PATENT DOCUMENTS

| | | | |
|---|---|---|---|
| 889,701 | 6/1908 | Luckenbach | 48/189.4 X |
| 1,154,868 | 9/1915 | McHenry . | |
| 1,926,627 | 9/1933 | Michaels | 48/189.4 |
| 2,645,463 | 7/1953 | Stearns . | |
| 2,816,518 | 12/1957 | Dagget . | |
| 2,890,868 | 6/1959 | Potchen . | |
| 3,089,683 | 5/1963 | Thomas et al. . | |
| 3,347,529 | 10/1967 | Hoppe et al. | 366/173 X |
| 3,674,740 | 7/1972 | Vernaleken et al. | 260/47 X |
| 3,897,935 | 8/1975 | Forster et al. . | |
| 3,905,395 | 9/1975 | Hype | 137/604 |
| 3,924,989 | 12/1975 | Althausen et al. | 425/130 |
| 4,074,363 | 2/1978 | Croft | 366/177 X |
| 4,133,485 | 1/1979 | Bouvin | 138/42 X |
| 4,202,635 | 5/1980 | Hendrickson | 366/162 |
| 4,209,258 | 6/1980 | Oakes | 366/161 X |

FOREIGN PATENT DOCUMENTS

| | | | |
|---|---|---|---|
| 507475 | 11/1954 | Canada | 48/189.6 |
| 859688 | 1/1961 | United Kingdom | 366/134 |

OTHER PUBLICATIONS

"Rotating Flow Mixing Device for Post Column Reaction in High Performance Liquid Chromatography", Shin-ichiro Kobayashi and Kazuhiro Imai, Anal. Chem., 52, 1548, (1980).

Primary Examiner—Philip R. Coe
Attorney, Agent, or Firm—L. E. Carnahan; Roger S. Gaither; Judson R. Hightower

[57] ABSTRACT

A gradient mixer which effects the continuous mixing of any two miscible solvents without excessive decay or dispersion of the resultant isocratic effluent or of a linear or exponential gradient. The two solvents are fed under low or high pressure by means of two high performance liquid chromatographic pumps. The mixer comprises a series of ultra-low dead volume stainless steel tubes and low dead volume chambers. The two solvent streams impinge head-on at high fluxes. This initial nonhomogeneous mixture is then passed through a chamber packed with spirally-wound wires which cause turbulent mixing thereby homogenizing the mixture with minimum "band-broadening".

9 Claims, 3 Drawing Figures

HIGH PRESSURE LIQUID CHROMATOGRAPHIC GRADIENT MIXER

BACKGROUND OF THE INVENTION

The U.S. Government has rights in this invention pursuant to Contract No. W-7405-ENG-48 between the University of California and the United States Department of Energy.

The present invention relates generally to an apparatus for a continuous flow mixing of any two miscible liquids, and more particularly to an apparatus wherein such mixing is effected with a linear or exponential gradient and without excessive decay or dispersion of the resultant isocratic effluent.

The continuous and complete intermixing of a plurality of liquids of solvents without creating a significant concentration gradient, is desirable for many industrial applications but presents many practical problems. In the use of high performance liquid chromatography, for instance, the efficient and rapid elution of compounds requires the gradual switchover from one solvent to another through a gradient, while maintaining a constant mobile phase flow rate. This usually produces gradients of increasing strength of the second solvent. These gradients are produced by creation of small "mixing chambers" within the two solvent phases.

Any mixing operation may be viewed as taking place in two steps or phases. In the initial phase, when the two liquids come into contact, there is an immediate but rough dispersion of one component in the other. In the second phase which follows, the liquid mixture is homogenized, i.e., the concentration gradients or differences created by the initial distribution are eliminated by the complete dispersion of one liquid in the other.

Mixing chambers available commercially, are normally expected to generate linear or exponential gradients. But even the so-called linear gradients usually have exponential characteristics due to the dilution caused by excessive void volumes in the mixing chamber. Exponential gradients are also similarly skewed. Therefore, a need exists for an efficient gradient mixer capable of handling both low and high pressure liquids.

SUMMARY OF THE INVENTION

The present invention fills the above-mentioned need by providing a high pressure liquid gradient mixer which has the capability of continuous and complete intermixing of a plurality of liquids.

Therefore, it is an object of this invention to provide a gradient mixer for liquids.

A further object of the invention is to provide a high pressure liquid gradient mixer.

Another object of the invention is to provide a liquid mixer that effects the continuous mixing of any two miscible solvents without excessive decay or dispersion of the resultant isocratic effluent, or linear or exponential gradient.

Another object of the invention is to provide a gradient mixer for a plurality of high pressure liquids which includes a series of ultra-low, dead volume tubes and low, dead volume chambers which include a chamber packed with spirally-wound wires.

The above objects are carried out by a high pressure liquid gradient mixer which produces accurate and precise linear or exponential gradients. Basically the gradient mixer of this invention involves the combination in series of a premixing tee, a premixing chamber, and a main mixing chamber with spirally wound wire therein, interconnected by appropriate reducing unions and narrow diameter components for providing high velocity liquid flow.

BRIEF DESCRIPTION OF THE DRAWINGS

The accompanying drawings which are incorporated herein and form a part of the specification, illustrate various aspects or embodiments of the invention, and together with the description, serve to explain the principles of the invention.

DETAILED DESCRIPTION OF THE INVENTION

The gradient mixer of the present invention consists broadly of a series of ultra-low, dead volume stainless steel tubes and low, dead volume chambers. In the operation of the instant gradienet mixer, two flowing solvents from two separate pumps are introduced at the two side or inlet arms of a premixing tee. The premixing tee has a single outlet or middle arm and the orifice ends of the inlet and outlet arms are constricted to have very small diameters so that the solvents flow at relatively high velocities due to high flux, especially at low flow rates.

Stagnant pools or eddies in the tubes are minimized by the provision of ferrules flush with the tubing ends. Complementary flows are utilized to produce constant flow rates for the solvents which impinge head on in the premixing tee and are carried by the middle arm of the premixing tee through a series of small-diameter components to a void volume chamber.

The void volume chamber also has a small inside diameter and serves as a void-volume pre-mixing chamber to provide initial blending of discrete solvent plugs. Since most high pressure liquid chromatographic (HPLC) pumps are of the reciprocating positive displacement type, a "constant flow" is achieved by repetitive pumping of small "plugs" of solvent. The pre-mixing thus facilitates later blending and homogenizing of the initial nonhomogeneous mixture. The void-volume pre-mixing chamber is coupled by means of small-diameter components to a main mixing chamber which comprises a plurality of spirally wound strands of stainless steel wire to create turbulent flow and to enhance mixing in a pseudo-laminar fashion. The void-volume pre-mixing chamber must be physically separated from the laminar mixing chamber in order to minimize eddy currents. The manner in which the spiral is wound provides no center void volume to the spiral. The spirally-wound wires cause turbulent mixing and the initial nonhomogeneous mixture which enters the main mixing chamber becomes homogenized with minimum band broadening. Other small-diameter components couple the main mixing chamber to a zero dead volume filter which exits to the column injection valve.

Although five and six strands of wire provided optimum results of the main mixing chamber, the number of strands is not limiting so long as no center void volume is created by too many wires being pulled together and proper contact and a tight fit between the strands of wire and the inside walls of the tube is not broken by the use of two few strands of wire.

Figure 1:
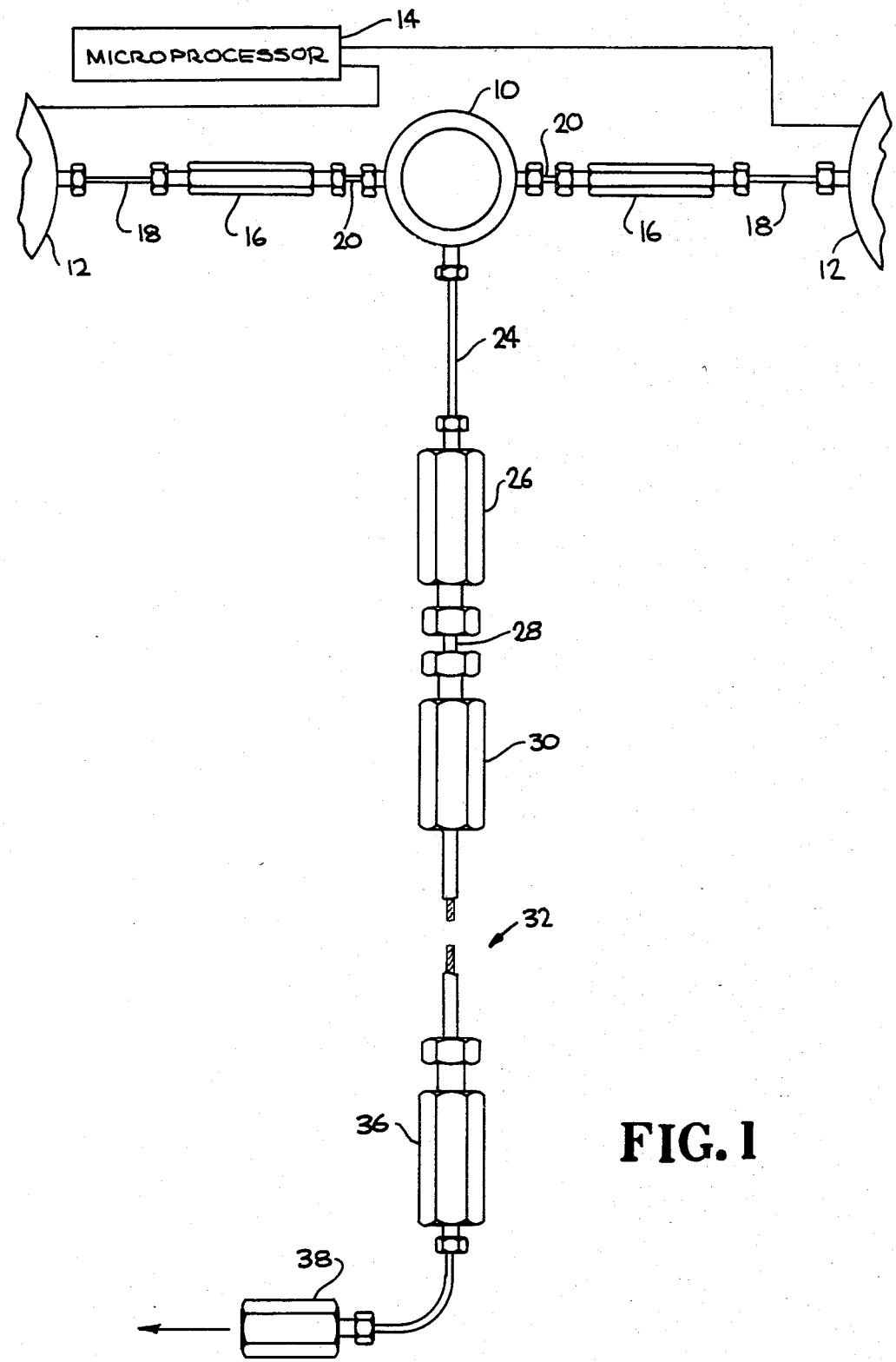
FIG. 1 is a schematic representation of an embodiment of the gradient mixer according to the present invention, showing the various components in their relative positions.

Referring now to the drawings, the embodiment of the gradient mixer of the instant invention, as shown in FIG. 1, consists of a zero void-volume premixing tee 10 with side arms 20 and middle arm 24. Delivery lines 18 are about 1/16th inch in outside diameter and are connected at one end to unions 16 and the other end to liquid chromatographic pumps 12. Pumps 12 are synchronized by microprocessor 14 known in the art, the details of which do not constitute part of the invention. Premixing tee 10 is connected to unions 16 through side arms 20, consisting of stainless steel tubes of 1/16th inch outside diameter and 0.01 inch inside diameter. Orifice ends 22 (see FIG. 2) of arms 20 that connect to premixing tee 10 are filed down to constrict the inside diameter to less than 0.005 inch. Middle or outlet arm 24 of premixing tee 10 is connected to reducing union 26 which in turn is connected to a void-volume premixing chamber 28 with a 2 mm inside diameter. Void-volume premixing chamber 28 in turn is connected through another ⅛ inch reducing union 30 to the main mixing chamber 32, described in detail hereinafter with respect to FIG. 3. Another reducing union 36 couples main mixing chamber 32 to a zero dead volume filter 38 which exits to a column injection valve, not shown.

Figure 2:
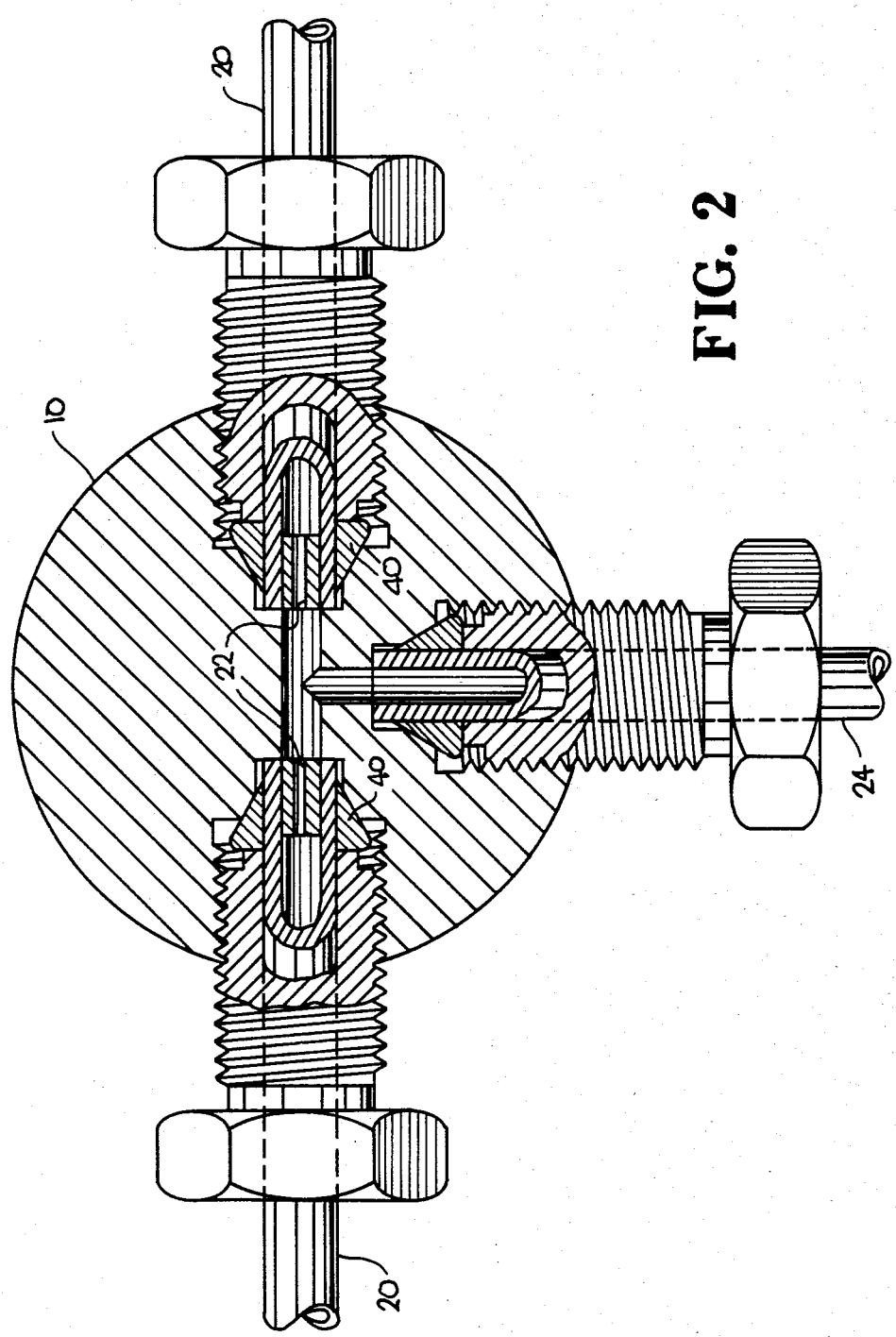
FIG. 2 is an enlarged frontal view, in cross-section, of the zero dead volume mixing tee of the gradient mixer of FIG. 1.

FIG. 2 is an enlarged cross sectional view of premixing tee 10 showing side arms 20 with constricted orifice ends 22 and middle or outlet arm 24. Ferrules 40 are provided at the constricted orifice ends 22 to be flush with the tubing ends and to insure that all three arms are connected so as to provide for zero dead volume.

Figure 3:
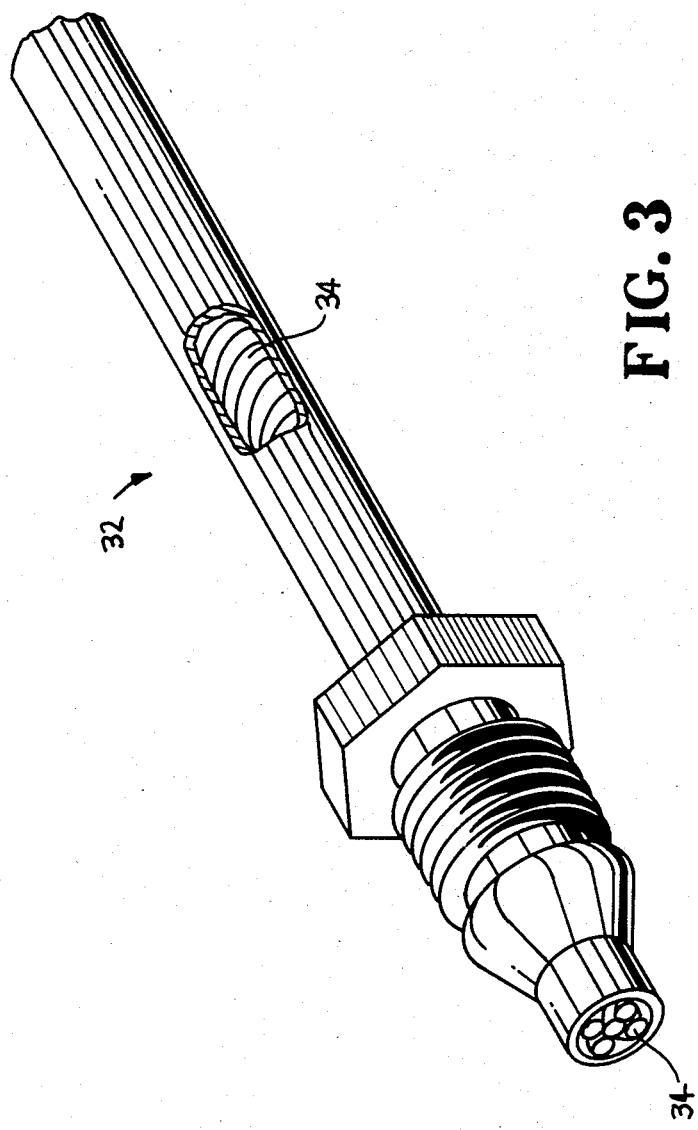
FIG. 3 shows the main mixing chamber of the gradient mixer of FIG. 1, with a portion cut away to show the spirally-wound strands of wire encased in a hollow stainless steel tube.

Main mixing chamber 32, as shown enlarged in FIG. 3, includes of a plurality of strands, preferably five or six, of stainless steel wires (five in this embodiment) that are run spirally within mixing chamber 32. The five spiral wires 0.026 inch in diameter, are first wound flush around a 0.05 inch mandrel. The mandrel is then removed and the wires pulled taut from both ends to create a spiral with no center void volume. The spiral is then inserted into chamber 32.

In operation of the embodiment of FIG. 1, two solvents are introduced at opposite sides of premixing tee 10 from pumps 12. The pumping rates, (exemplified as near zero to 10 ml/min at pressures of several hundred to about 5,000 psi) of the two solvent delivery pumps are synchronized by microprocessor 14 to provide an increasing flow rate from one or the other of the pumps. The junctures between unions 16 and side arms 20 are constructed to have very small diameters so that the solvents flow at various velocities (exemplified as near zero to 1316 cm/sec.) due to high flux, especially at low flow rates, such as 65.8 cm/sec. for a pumping rate of 0.5 ml/min. Complementary flows are utilized to produce constant flow rates for the solvents which impinge head on in premixing tee 10 and are carried by middle arm 24 of tee 10 through reducing union 26 to premixing chamber 28. Premixing chamber 28 serves as a void-volume premixing chamber to provide initial blending of discrete solvent plugs. As pointed out above, most HPLC pumps are of reciprocating positive displacement type and a "constant flow" is achieved by repetitive pumping of small "plugs" of solvent, and this premixing in tee 10 facilitates later blending and homogenizing of the initial nonhomogeneous mixture.

Union 30 couples the void-volume pre-mixing chamber to the main mixing chamber 32 which includes a plurality of spirally wound strands of wire 34 to create turbulent flow and to enhance mixing in a pseudo-laminar fashion. The manner in which the spiral is wound provides no center void volume to the spiral. Reducing union 36 couples main mixing chamber 32 to a zero dead volume filter which exists to the column injection valve.

It has thus been shown that the present invention provides a high pressure liquid chromatographic gradient mixer capable of continuous mixing of any two miscible solvents without excessive decay or dispersion of the resultant isocratic effluent, or linear or exponential gradient.

While a particular embodiment of the present invention has been illustrated and described, modifications will become apparent to those skilled in the art, and it is intended to cover in the appended claims all such modification as come within the scope of the invention.

What is claimed is:

1. A liquid gradient mixer comprising:
   a premixing tee adapted to receive liquid under pressure from a plurality of sources;
   a premixing chamber operatively connected to receive a liquid mixture from said premixing tee; and
   a main mixing chamber operatively connected to receive the liquid mixture from said premixing chamber, said main mixing chamber being provided with means for providing a no center void therein, said means comprising a housing having a plurality of spiral wound wires extending longitudinally through said housing which cause turbulent mixing of the liquid mixture so as to homogenize the liquid mixture discharging therefrom,
   said plurality of spiral wound wires being positioned within said housing so as to provide the no center void within said housing.

2. The liquid gradient mixer of claim 1, wherein said premixing tee includes a plurality of members for connecting said tee to an associated liquid source and to said premixing chamber, said members being provided with constricted inner orifice ends about which are positioned ferrules to insure zero dead volume at the inner ends of said members.

3. The liquid gradient mixer of claim 1, wherein said premixing tee is connected to receive liquid under pressure from a plurality of pumps, said plurality of pumps being controlled and synchronized by a microprocessor.

4. The liquid gradient mixer of claim 1, wherein said premixing chamber is of a void-volume type.

5. The liquid gradient mixer of claim 4, wherein said premixing chamber has a diameter of about 2 mm.

6. The liquid gradient mixer of claim 1, wherein said plurality of spiral wound wires consists of five wires, said wires being positioned in said housing so as to have proper contact and a tight fit between said wires and an inside wall of said housing to provide the no center void volume within said housing.

7. In a liquid gradient mixer, a premixing tee having a housing defining a T-shaped chamber therein, a plurality of inlet members for connecting said tee to associated liquid sources via a pair of oppositely located arms of said T-shaped chamber, and an outlet member connected to a middle arm of said T-shaped chamber for connecting liquid passing through said tee to a point of use, each of said inlet members being provided with means for insuring a zero dead volume at the inner ends thereof, said means comprising a constricted inner orifice about which is positioned a ferrule to insure the zero dead volume at the inner ends of said inlet members.

8. A mixing chamber operatively connected to receive liquid for homogenious mixing therein, and operatively connected to discharge a mixture of liquid therefrom, said mixing chamber being provided with means for providing a no center void volume within said mixing chamber, said means consisting of a casing having a plurality of spirally wound members extending longitudinally through at least said casing and positioned so as to have contact and a tight fit between said members and an inside wall of said casing to provide the no center void volume within at least said casing and which cause turbulent mixing of the liquid so as to homogenize the liquid mixture discharging from said mixing chamber.

9. The mixing chamber of claim 8, wherein said plurality of spiral wound members comprises five spiral wound wires.

* * * * *